United States Patent [19]

Frater et al.

[11] Patent Number: 5,403,944
[45] Date of Patent: Apr. 4, 1995

[54] ORGANOSILICON COMPOUNDS

[75] Inventors: Georg Frater; Rolf Schwarzenbach, both of Winterthur, Switzerland; Stephane F. M. Van Oycke, South Glamorgan, Great Britain

[73] Assignee: Givaudan-Roure Corporation, Clifton, N.J.

[21] Appl. No.: 960,384
[22] PCT Filed: May 7, 1992
[86] PCT No.: PCT/EP92/01001
  § 371 Date: Jan. 7, 1993
  § 102(e) Date: Jan. 7, 1993
[87] PCT Pub. No.: WO92/20690
  PCT Pub. Date: Nov. 26, 1992

[30] Foreign Application Priority Data
May 10, 1991 [GB] United Kingdom ............ 9110123

[51] Int. Cl.$^6$ .............................................. C07F 7/08
[52] U.S. Cl. ................................................. 556/441
[58] Field of Search .................................... 556/441

[56] References Cited

U.S. PATENT DOCUMENTS

| | | | |
|---|---|---|---|
| 3,718,681 | 2/1973 | Adams | 556/441 |
| 3,962,299 | 6/1976 | Stackman | 556/441 |
| 4,176,124 | 11/1979 | Darms et al. | 556/441 X |
| 4,924,020 | 5/1990 | Okawa et al. | 556/441 |
| 4,992,261 | 2/1991 | Colas et al. | 556/441 X |
| 5,053,290 | 10/1991 | Canivenc et al. | 556/441 X |
| 5,077,422 | 12/1991 | Colas et al. | 556/441 X |
| 5,138,012 | 8/1992 | Riding et al. | 556/441 X |

FOREIGN PATENT DOCUMENTS 0305059 3/1989 European Pat. Off. .
0350314 1/1990 European Pat. Off. .
0358584 3/1990 European Pat. Off. .
0392882 10/1990 European Pat. Off. .

*Primary Examiner*—Paul F. Shaver
*Attorney, Agent, or Firm*—George M. Gould; George W. Johnston

[57] ABSTRACT

Novel organosiloxane compounds have at least one unit $$O_{\frac{3-a}{2}}Si(R)_a-C(R^1)=CH-(CR_2^1)_n-O- \quad (i)$$

$$C_6R_2^2H_2-CH=C-[C(O)OR^3]_2$$

any other units being present in this organosiloxane are $$R_b''SiO_{\frac{4-b}{2}}, \quad (ii)$$

wherein R is a $C_{1-8}$ alkyl or aryl, $R^1$ is H or a $C_{1-5}$ alkyl, $R^2$ is H, $C_{1-5}$ alkyl or $OR^1$, $R^3$ is a $C_{1-5}$ alkyl, $R''$ is H, a monovalent $C_{1-8}$ hydrocarbon or halogenated hydrocarbon group, a is 0, 1 or 2, b 0, 1, 2 or 3 and n 1 to 6, provided the $$-C(R^1)=CH-(CR^1_2)_n-O-$$

group and the two $R^2$ groups are linked to the aromatic ting at the para- and meta-positions in relation to the group $-CH=C[C(O)OR^3]_2$.

The compounds are useful as UV sunscreens. Compositions containing them are also included.

16 Claims, No Drawings

ORGANOSILICON COMPOUNDS

This invention is concerned with novel organosilicon compounds which are effective in absorbing ultra violet radiation and is also concerned with a process of preparing such compounds.

A number of organic compounds, generally organic acids and derivatives thereof, are known to be chromophores having U.V.-absorbing properties and are employed on a commercial scale as ingredients in sunscreen preparations or as plastic additives. Although such materials function adequately they are easily removed from the substrate to which they have been applied. For example, cosmetic sunscreen preparations can be removed during bathing thus requiring repeated applications if protection is to be maintained. It is also desirable that the active ingredient remain on the surface of the skin rather than penetrate into or through the skin.

Compounds which overcome this problem to a certain extent are disclosed for example in European Patent Specification 305 059, which provides organosilicon compounds having at least one unit of the general formula

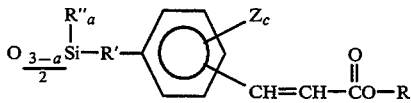

any other units present in the said siloxanes being those represented by the general formula

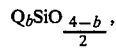

wherein R represents a $C_{1-18}$ alkyl group, R' is a divalent alkylene or oxyalkylene group having from 2 to about 20 carbon atoms, or a divalent alkenylene or oxyalkenylene group having from 2 to 20 carbon atoms, wherein the carbon-carbon double bond is adjacent to the silicon atom, R" is a halogen atom, an alkyl, aryl, alkoxy or alkoxyalkoxy group having less than 9 carbon atoms, Q represents a hydrogen atom, a monovalent $C_{1-18}$ hydrocarbon or halogenated hydrocarbon group, Z is an alkyl or an alkoxy group having from 1 to 8 carbon atoms or a hydroxyl group, a and b each have a value of 0, 1, 2 or 3 and c is 0 or 1, provided that at least one of Z and R' is linked to the multivalent aryl group via an ether linkage.

It was found, however, that although the materials described above were, in comparison with the prior art, less susceptible to hydrolysis at the ester linkage, for example by enzymatic hydrolysis on the skin when these materials were used as cosmetic sunscreen agents, they were not sufficiently photostable when exposed to UV irradiation.

EP publication 392 882 discloses the use of diorganopolysiloxanes with a benzalmalonate functionality in cosmetic applications. The diorgano-polysiloxanes which are useful in said application have the average general formula

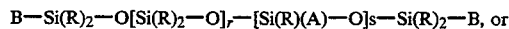

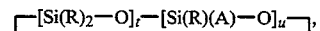

wherein R is $C_{1-10}$ alkyl, phenyl or trifluoropropyl, B is R or A, r is from 0 to 200, s is from 0 to 50, u is from 1 to 20, t is from 0 to 20, t+u is at least 3, there being at least one group A per molecule and A denotes a structure of the general formula

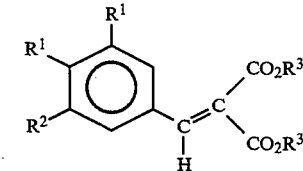

wherein $R^1$ is H, OH, trimethylsiloxy, $C_{1-6}$ alkoxy or a divalent group $—(O)_n—(CH_2)_p—CH(R'')—CH_2—$, n is 0 or 1, p is 1 to 10, R" is H or $C_{1-4}$ alkyl, $R^2$ is H, $C_{1-6}$ alkyl or $C_{1-6}$ alkoxy, $R^3$ is $C_{1-8}$ alkyl, at least one of the $R^1$ groups being the divalent group.

We have found that although the materials described in both above identified references perform well in many applications, and although there is a reduction in the amount of chromophore which penetrates through the skin when applied thereto in comparison with the amount of chromophore which penetrates when it has been applied as a pure compound (i.e. not linked to an organosilicon compound), there is still a need to further reduce the amount of penetration through the skin.

We have now found that if certain novel chromophores are used in the preparation of organosilicon compounds, improved cosmetic preparations, effective in absorbing ultra violet radiation can be obtained.

According to a first aspect of the invention there is provided an organosiloxane compound having at least one unit of the general formula

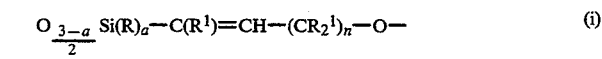

any other units present in the said siloxanes being those represented by the general formula

wherein R represents a $C_{1-8}$ alkyl or an aryl group, $R^1$ is a hydrogen atom or a $C_{1-5}$ alkyl group, $R^2$ is a hydrogen atom, a $C_{1-5}$ alkyl group or a group $OR^1$, $R^3$ is a $C_{1-5}$ alkyl group, R" represents a hydrogen atom, a monovalent $C_{1-8}$ hydrocarbon or halogenated hydrocarbon group, a has a value of 0, 1 or 2, b has a value of 0, 1, 2 or 3 and n has a value of from 1 to 6, provided that the

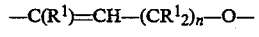

group and the two $R^2$ groups are linked to the aromatic ring at the para and both meta positions in relation to the group

In the general formula of the organosilicon compounds of the invention R may be for example methyl, ethyl, butyl or phenyl. R" is hydrogen or a monovalent hydrocarbon or halogenated hydrocarbon group having less than 8 carbon atoms, for example alkyl, alkenyl, aryl, alkaryl, aralkyl and halogen substituted alkyl, alkenyl, aryl, alkaryl and aralkyl groups. Examples include methyl, ethyl, vinyl, phenyl and 3,3,3- trifluoropropyl. $R^3$ denotes alkyl groups having up to 5 carbon atoms for example methyl, ethyl, propyl, isopropyl, butyl, secondary butyl, isobutyl, pentyl and neopentyl. $R^1$ is either a group $R^3$ or a hydrogen atom and $R^2$ is a group $R^1$ or a group $OR^1$. It is preferred that at least 80% of all R and R" groups are methyl groups, most preferably substantially all R and R" groups are methyl groups. It is also preferred that $R^1$ is either hydrogen, methyl or ethyl, most preferably hydrogen. Preferably each $R^2$ group is H or one $R^2$ group is a hydrogen, while the other one is an alkoxy group, preferably methoxy or ethoxy. $R^3$ is preferably methyl or ethyl. a is preferably 1 while b is preferably 2, making the organosilicon compound a substantially linear or cyclic diorgano-siloxane polymer. However, if the diorganosiloxane is a substantially linear polymer at least two endblocking units must be present, thus requiring the presence of 2 units in which a has a value of 2, two units in which the value of b is 3 or one unit wherein a is 2 and one unit in which b is 3. n is preferably 1, 2 or 3. Suitable preferred polymers have therefore either the general formula

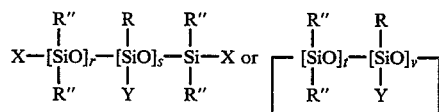

wherein R and R" are as defined above, X denotes a group Y or a group R" and Y denotes a group of the formula

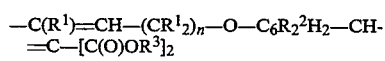

$-C(R^1)=CH-(CR^1{}_2)_n-O-C_6R_2{}^2H_2-CH-$
$=C-[C(O)OR^3]_2$ r has a value of from 0 to 100, s has a value of from 0 to 20, whereby at least one X denotes Y in the case that s=0, t has a value of from 0 to 10, v has a value of from 1 to 10 and v+t has a value of at least 3.

In the substituent Y of the organosilicon compounds according to the invention, the group

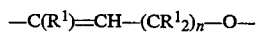

$-C(R^1)=CH-(CR^1{}_2)_n-O-$ may occupy the meta-position or the para-position of the aromatic ring in relation to the group $-CH=C[C(O)OR^3]_2$. Preferably the para-position is thus occupied. The groups $R^2$ occupy the remaining two positions out of the para- and meta-positions in relation to the group $-CH=C[C(O)OR^3]_2$. Examples of preferred substituents Y thus include

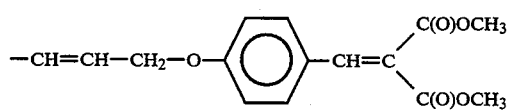

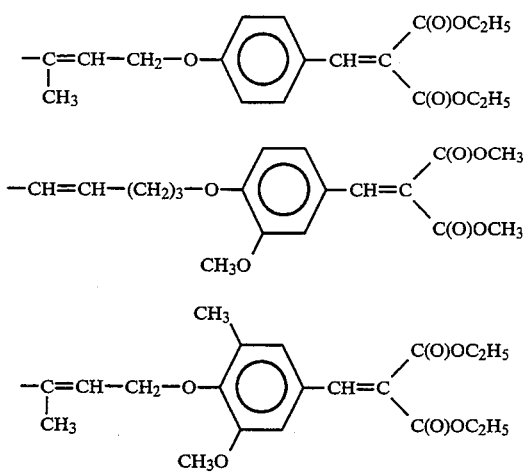

The organosilicon compounds of the present invention have at least one unit falling within the general formula (i), preferably at least 2. Suitable organosilicon compounds are polymeric materials which may be homopolymers consisting only of such units (i), or they may be copolymers containing both units (i) and units having the general formula (ii). The organosilicon compounds may vary from freely flowing liquids to highly viscous gum-like materials or resinous solids. Preferred, at least for cosmetic applications, are the liquid substantially linear organosiloxane homopolymers and copolymers, for example those having a viscosity of from 100 to 20000 m²/s, more prefer- ably 500 to 5000 mm²/s as these are more easily mixed with other ingredients to make cosmetic compositions and as they will spread more easily onto the skin.

Organosilicon compounds of the invention which are especially preferred are those wherein the number of units (i) is limited to a maximum of 20% of the total number of siloxane units in the molecule. For maximum efficiency in its U.V. absorbing property it is preferred that the number of units (i) be limited to 10% or less of the total. The units of formula (i) may be distributed randomly in an organosiloxane polymer, they may be end-blocking units of the polymer or they may be located at the end of the poly-mer and pending in chain of the polymer at the same time. Units of the general formula (i) are preferably situated at the end of the organo-siloxane polymer forming one or more endblocking units of the polymer. In the most preferred organosilicon compounds which are substantially linear polyorganosiloxane polymers, both endblocking units have a structure represented by the general formula (i), while all other units are according to the general formula (ii). The most preferred organosilicon compounds have two units of the formula (i) and a larger number of units according to the general formula (ii), e.g. 8 to 90, especially 8 to 40.

The organosilicon compounds according to the invention are effective in absorbing ultra violet radiation in the erythemic region (290–320 nm) which makes them particul-arly suitable for use in cosmetic sunscreen preparations where absorption in the UV-B region is particularly desirable. Most preferred for this application are those that have a maximum absorbance at 300-320 nm.

The organosilicon compounds of the present invention can, quite generally, be prepared by the reaction of an organosilicon compound in which each unit (i) is replaced with a unit having the general formula

 (iv)

with a chromophore of the general formula

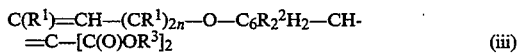 (iii)

These chromophores are in themselves novel compounds and the invention therefore includes in one of its aspects a compound of the formula

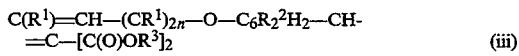 (iii)

wherein $R^1$ is a hydrogen atom or a $C_{1-5}$ alkyl group, $R^2$ is a hydrogen atom, a $C_{1-5}$ alkyl group or a group $OR^1$, $R^3$ is a $C_{1-5}$ alkyl group and n has a value of from 1 to 6, provided that the group containing the unsaturated carbon-carbon triple bond and the two $R^2$ groups are linked to the two meta-positions and to the para-position of the aromatic ring in relation to the ester containing group.

Compounds of the general formula (iii) may be prepared e.g. by reacting a hydroxy or dihydroxy benzaldehyde with halogenopropyne, followed by a further reaction with a diester of malonic acid. The first reaction is preferably carried out in the presence of a suitable solvent, e.g. acetone, preferably at reflux temperatures. The presence of a catalyst is also preferred. The second reaction is also preferably carried out in the presence of a solvent, e.g. toluene at reflux temperatures. The final product of formula (iii) is a light brown crystal.

The invention also includes a process for the preparation of organosilicon compounds of the kind specified herein, which comprises reacting together
(A) a compound of the general formula

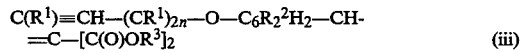 (iii)

wherein $R^1$ is a hydrogen atom or a $C_{1-5}$ alkyl group, $R^2$ is a hydrogen atom, a $C_{1-5}$ alkyl group or a group $OR^1$, $R^3$ is a $C_{1-5}$ alkyl group and n has a value of from 1 to 6, provided that the group containing the unsaturated triple bond and the two $R^2$ groups are linked to the two meta-positions and to the para-position of the aromatic ring in relation to the group —CH=C—[C(O)OR³]₂ and
(B) an organosilicon compound having at least one unit of the general formula

 (iv)

any other units present in the organosilicon compound being those represented by the general formula

 (ii)

wherein R, R″, a and b are as hereinabove defined.

The reaction is preferably carried out employing stoichiometric proportions of (A) and (B) or a slight stoichiometric excess of (A). However, a stoichiometric deficiency of (A) can be employed if residual silicon-bonded hydrogen is desired in the product.

Alternatively polymeric organosilicon compounds of the invention can also be obtained by first preparing the corresponding hydrolysable silane, employing in place of the organosilicon compound (B) the corresponding SiH containing silane (C) which has the general formula

 (v)

wherein R is as defined above, Z is a hydrolysable group, preferably alkoxy having 1 to 8 carbon atoms and x has a value of 0, 1 or 2.

The silane (D) resulting from this reaction may be submitted thereafter to cohydrolysis with a further hydrolysable silane or equilibration with (E) cyclic or (F) linear polyorganosiloxanes consisting essentially of units of the formula (ii). Silanes (D) which can be used in this method are novel in themselves and are included in the scope of the present invention. Silanes (D) have the general formula

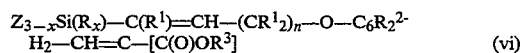 (vi)

wherein R, $R^1$, $R^2$, $R^3$, Z, x and n are as defined above.

Thus, in more detail, the process comprises
I) the preparation of a hydrolysable silane by reacting a silane of the general formula

 (v)

wherein R represents a $C_{1-8}$ alkyl or aryl group, Z is a hydrolysable group and x has a value of 0, 1 or 2, with a compound of the general formula

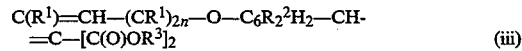 (iii)

wherein $R^1$ is a hydrogen atom or a $C_{1-5}$ alkyl group, $R^2$ is a hydrogen atom, a $C_{1-5}$ alkyl group or a group $OR^1$, $R^3$ is a $C_{1-5}$ alkyl group and n has a value of from 1 to 6, provided that the group containing the unsaturated triple bond and the two $R^2$ groups are linked to the two meta-positions and to the para-position of the aromatic ring in relation to the group —CH=C—[C(O)OR³]₂, and
II) submitting the hydrolysable silane to cohydrolysis or equilibration with cyclic or linear polydiorganosiloxanes consisting essentially of units of the formula

 (ii)

wherein R″ represents a hydrogen atom a monovalent $C_{1-8}$ hydrocarbon or halogenated hydrocarbon, and b has a value of 0, 1, 2 or 3.
Z is preferably an alkoxy group having from 1 to 8 carbon atoms.
As concerns the cohydrolysis, such reaction will conveniently be in conjunction with other hydrolysable silanes (e.g. diorganodihalosilanes, or diorgano-alkoxysilanols, etc.) or with siloxanes having hydrolysable endgroups (e.g. α,w dihydroxy polydimethylsiloxanes).

As concerns the equilibrium aspect on the linear or cyclic polydiorganosiloxanes, cyclic siloxanes will conveniently have the general formula $[R^2SiO]_n$, wherein n has a value of from 3 to 9, and linear polydiorganosiloxanes are usually used as end-blocking units, and will be short chain triorganosiloxane end-blocked polydiorgano-siloxanes (in the shortest form hexaorganodisiloxane $[R_3Si—O—SiR_3]$).

This alternative process involves thus technique which is known per se.

In order to obtain the particularly preferred polymeric organosilicon compounds of the invention the reaction is carded out in such a way that in the reaction product at least one siloxane unit and no more than 20% of the total number of siloxane units has a structure according to formula (i). This may be achieved by reacting polymeric organosilicon compounds (B) which have a maximum of 20 mole % silicon-bonded hydrogen atoms, with stoichiometric amounts of compound (A). Excess amounts of (A) may also be used in this case. If residual SiH groups are desired in the organosilicon compound product less than stoichiometric amounts of compound (A) may be employed. The particularly preferred polymeric organosilicon compounds of the invention may also be obtained by reacting polymeric organosilicon compounds (B) having more than 20 mole % silicon-bonded hydrogen atoms, with less than stoichiometric amounts of compound (A). Most preferably, however, organosilicon compounds (B) are employed which are polydiorganosiloxanes endblocked with diorganohydrosiloxane units provided the siloxane has a minimum chain length of 10 silicon atoms.

The reaction between (A) and (B) may be carried out employing known procedures for the addition of silicon-bonded hydrogen atoms to groups containing aliphatic unsaturation. Thus, such reactions are generally catalysed by a platinum group metal or a compound or complex of such a metal. Examples of catalysts which may be employed in the reaction between (A) and (B) are platinum on carbon, chloroplatinic acid, platinum acetyl acetonate, complexes of platinum compounds with unsaturated compounds e.g. olefins and vinyl siloxanes, complexes of rhodium and palladium compounds and complexes of platinum compounds supported on inorganic substrates. The addition reaction may be performed at reduced, atmospheric or increased pressure. It is generally preferred to employ a solvent e.g. toluene or xylene in the reaction mixture although the presence of a solvent is not essential. It is also preferred to carry the reaction out at elevated reaction temperatures e.g. from about 50° C. up to the reflux temperature of the reaction mixture.

The organosilicon compounds of this invention have similar UV absorbance characteristics to those disclosed in the prior art. They are useful as agents for preventing sunburn and are thus useful in skin care and hair care applications. They may be applied per se to the skin or hair but are more preferably formulated into cosmetic compositions with, for example, inert carriers e.g. solvents such as water, ethanol, isopropanol, glycerine and mineral oil and cream base materials such as stearic acid, propylene glycol, beeswax and cetyl alcohol. Other conventional ingredients e.g. perfumes and known U.V. absorbing substances may also be included in the formulated compositions. The organosilicon compounds of the present invention are also useful in the coating of substrates e.g. wood, plastics or metal, to which they may be applied either per se or as additives to coating compositions or they may be incor- porated as addit-ives in plastics materials.

The following examples, in which parts and percentages are expressed by weight illustrate the invention.

EXAMPLE 1

Preparation of propanedioic {[4-(2-propynyloxy)phenyl]methylene}-diethyl ester (the most preferred compound)

To a stirred suspension of 4-hydroxybenzaldehyde (425.8 g) and $K_2CO_3$ (807.6 g) in acetone (2,960 ml) at reflux temper-ature of about 60° C. under a nitrogen atmosphere, was added dropwise 3-bromo-propyne (502.4 g) over a period of 2 hours. The reaction was heated at reflux for 3 more hours. After cooling to room temperature the reaction mixture was filtered and the excess of $K_2CO_3$ removed and washed several times with acetone. The filtrate was washed with saturated aqueous solution of $NaHCO_3$ and NaCl. The aqueous phase was extracted with diethyl ether. The combined organic extracts were dried over $Na_2SO_4$, filtered and concentrated to a volume of 1 liter. The solution was kept in the refrigerator overnight. The crystals were filtered out and washed with cold diethyl ether. The filtrate was kept in the refrigerator and some more crystals were formed and removed. This procedure was repeated 3 times resulting in 1,385.26 g of 4-(2-propynyloxy) benzaldehyde in 83% yield. The material was analysed by gas chromatography, and shown to be 99.9% pure. Infrared and mass spectroscopic analysis confirmed the structure.

The resulting compound (449.2 g) was added in small amounts to a stirred solution of diethyl malonate (448.5 g), piperidine (23.84 g), toluene (1,400 ml) and acetic acid (59 g) at about 50° C. The acetic acid had been added in three equal portions after 1, 1.5 and 2 hours respectively. The reaction mixture was heated to reflux. After four hours the mixture was allowed to cool to room temperature and washed with saturated aqueous solution of $NaHCO_3$ and NaCl, dried with $Na_2SO_4$, filtered and concentrated, giving 853.4g of a dark brown oily product. Diethyl ether (458 ml) and n-hexane (358 ml) were added and the solution kept in a refrigerator overnight. The solution was filtered, giving 564.8 g of light brown crystals (67% yield) having a melt-ing point of 45.5° to 48° C. Recrystallisation in ethanol and n-hexane yielded 543 g of the title compound as light brown crystals. Analysis revealed a melting point of 48.5° to 49.5° C. and a purity by capillary gas chromatography of 99.9%.

EXAMPLE 2

Preparation of propanedioic {[4-(2-propynyloxy)phenyl]methylene}-dimethyl ester

The procedure of the above method was repeated except that dimethyl malonate was used instead of diethyl malonate.

EXAMPLE 3

5 g of {[4-(2-propynyloxy)phenyl]methylene}-diethyl ester were dissolved in 20 g of toluene and heated under nitrogen to about 80° C. 13.2 g of a hydrosiloxane having a degree of polymerisation of 20 and 10 mpc SiH groups (3.62% SiH) were then added dropwise after a platinum complex was also added, giving $10^{-4}$ mole of Pt per mole of SiH of the hydro-siloxane. The mixture was heated to reflux and maintained until all SiH had disappeared of the infrared spectroscopic analysis. It was then allowed to cool to room temperature. The toluene was then evaporated to leave after washing 16.5 g of a slightly brown polymer having the average structure R—[(CH$_3$)$_2$SiO]$_{20}$—R, wherein R has the formula

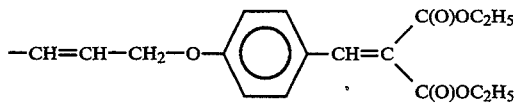

Only 1.6% by weight of the total reaction product of unreacted {[4-(2-propynyloxy)phenyl]methylene}-diethyl ester was present in the endproduct.

EXAMPLE 4

10 g of {[4-(2-propynyloxy)phenyl]methylene}-diethyl ester were dissolved in 10 g of toluene and heated under nitrogen to about 80° C. 13.2 g of a hydrosiloxane having a degree of polymerisation of 100 and 20 mpc SiH groups (8.43% SiH) were then added dropwise after a platinum complex was also added, giving 10$^{-4}$ mole of Pt per mole of SiH of the hydrosiloxane. The mixture was heated to reflux and maintained until all SiH had disappeared of the infrared spectroscopic analysis. It was then allowed to cool to room temperature. The toluene was then evaporated to leave after washing 21.2 g of a hazy, very viscous polymer having the average structure

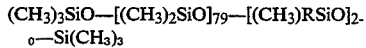

wherein R has the formula

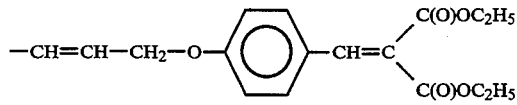

EXAMPLES 5 and 6

Similar procedures as described for Examples 3 and 4 were used to make polymers with the average formulae (5) R—[(CH$_3$)$_2$SiO]$_2$—R wherein R has the formula

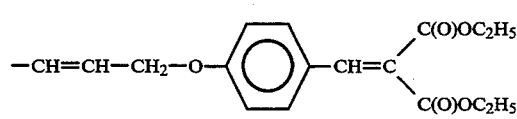

(6) (CH$_3$)$_3$SiO—[(CH$_3$)$_2$SiO]$_6$—[(CH$_3$)RSiO]-$_2$—Si(CH$_3$)$_3$ wherein R has the formula

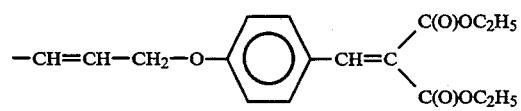

Comparative Example 1

A similar procedure as described for Examples 3 and 4 was used to make a polymer with the average formula

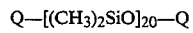

Q—[(CH$_3$)$_2$SiO]$_{20}$—Q wherein Q has the formula

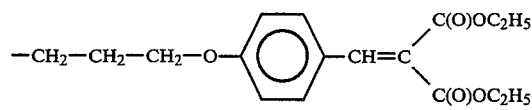

3.3% by weight of the total reaction product of unreacted {[4-(2-allyloxy)phenyl]methylene}-diethyl ester was present in the endproduct.

Comparative Example 2

A similar procedure as described for Examples 3 and 4 was used to make a polymer with the average formula

(CH$_3$)$_3$SiO—Si(CH$_3$)Z—OSi(CH$_3$)$_3$, wherein Z has the formula

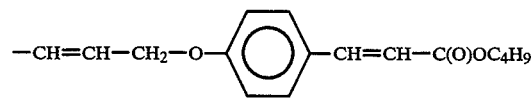

Comparative Example 3

Commercially available Parsol MCX was used which has the formula

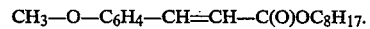

CH$_3$—O—C$_6$H$_4$—CH=CH—C(O)OC$_8$H$_{17}$.

UV Absorption Tests

Comparative Example 1 and Example 1 were both tested for their absorption at 300 nm (E 1%,cm). To this effect the samples were dissolved in tetrahydrofuran. Example 1 showed an absorption of 211 while Comparative Example 1 only gave a value of 83. This shows that the organosilicon compounds according to the invention are better than the prior art.

Stability and Water Resistance

Each sample was tested and found satisfactory in view of the stability to UV radiation and its resistance to washing off with water.

Skin Penetration Tests

Invitro penetration tests were carried out on rat skin. The samples were dissolved in tetrahydrofuran at a concen-tration of 10%, and this was applied to the skin at a dosage of 30 μl per 5 cm$^2$ and penetration was checked after 16 hours. After the test the penetration level was inspected by measuring the amount of material on the skin surface, in the horny layer, in the upper part of the skin, in the lower part of the skin and in the chamber (vitro). This was tested by wiping the surface to remove all non-penetrated material and placing it in a glass vial, followed by stripping the cleaned skin several times with adhesive tape to remove the horny layer and placing the tapes in a second glass vial. The stripped skin was then divided in an upper and lower part. The upper part was homogenised in 10 ml of tetrahydrofuran and placed in a third vial, while the lower part was treated separately in the same way and placed in a fourth vial. The chamber liquid was then placed in a fifth vial, the chamber rinsed with tetrahydrofuran which was also added to the vial.

The content of each of the vials was then extracted with tetrahydrofuran and analysed by high performance liquid chromatography. The most preferred materials are those where the amount of penetration in the lower skin is minimal. The results, based on an average from 2 experiments each, are shown in Table I.

TABLE I

| Example | Skin penetration values in % | | | | |
|---|---|---|---|---|---|
| | Skin surface | Horny layer | Upper skin | Lower skin | Chamber liquid |
| 3 | 90.7 | 1.6 | 7.5 | 0.2 | <0.1 |
| 4 | 73.7 | 24.0 | 2.1 | 0.2 | <0.1 |
| 5 | 89.4 | 6.7 | 3.5 | 0.4 | <0.1 |
| 6 | 98.5 | 3.2 | 0.9 | 0.4 | <0.1 |
| Comp. 1 | 88.9 | 6.1 | 3.3 | 1.7 | <0.1 |
| Comp. 2 | 52.2 | 6.8 | 7.8 | 3.2 | <0.1 |
| Comp. 3 | 46.3 | 3.0 | 8.5 | 2.8 | 9.4 |

It is clear that materials according to the invention have less penetration through the skin than prior art materials.

We claim:

1. An organosiloxane compound having at least one unit of the general formula

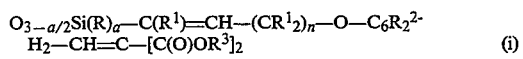
$$O_{3-a/2}Si(R)_a\text{---}C(R^1)\text{==}CH\text{---}(CR^1{}_2)_n\text{---}O\text{---}C_6R_2{}^2H_2\text{---}CH\text{==}C\text{---}[C(O)OR^3]_2 \quad (i)$$

any other units present in the said siloxanes being those represented by the general formula

$$R_b{}''SiO_{\frac{4-b}{2}} \quad (ii)$$

wherein R represents a $C_{1-8}$ alkyl or an aryl group, $R^1$ is a hydrogen atom or a $C_{1-5}$ alkyl group, $R^2$ is a hydrogen atom, a $C_{1-5}$ alkyl group or a group $OR^1$, $R^3$ is a $C_{1-5}$ alkyl group, R" represents a hydrogen atom, a monovalent $C_{1-8}$ hydrocarbon or halogenated hydrocarbon group, a has a value of 0, 1 or 2, b has a value of 0, 1, 2 or 3 and n has a value of from 1 to 6, provided that the

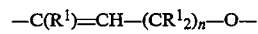
$$\text{---}C(R^1)\text{==}CH\text{---}(CR^1{}_2)_n\text{---}O\text{---}$$

group and the two $R^2$ groups are linked to the aromatic ring at the para- and both meta-positions in relation to the group —CH==C[C(O)OR$^3$]$_2$.

2. An organosiloxane compound according to claim 1 wherein at least 80% of all R, and R" groups are methyl groups.

3. An organosiloxane compound according to claim 1 wherein each $R^1$ is selected from hydrogen, methyl and ethyl.

4. An organosiloxane compound according to claim 1 wherein at least one $R^2$ group is a hydrogen, the other being hydrogen, methoxy or ethoxy.

5. An organosiloxane compound according to claim 1 wherein $R^3$ is methyl or ethyl.

6. An organosiloxane compound according to claim 1 wherein each $R^1$ and $R^2$ group is hydrogen.

7. An organosiloxane compound according to claim 1 which is a substantially linear or cyclic diorganosiloxane polymer.

8. An organosiloxane compound according to claim 1 wherein the group

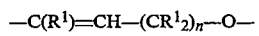
$$\text{---}C(R^1)\text{==}CH\text{---}(CR^1{}_2)_n\text{---}O\text{---}$$

occupies the para-position on the aromatic ring in relation to the group —CH—C(C(O)OR$^3$)$_2$, and both groups $R^2$ occupy the meta-positions on the aromatic ring in relation to the group —CH==C(C(O)OR$^3$)$_2$.

9. An organosiloxane compound according to claim 1 wherein the number of units (i) is limited to a maximum of 20% of the total number of siloxane units in the molecule.

10. An organosiloxane compound according to claim 9 wherein the number of units (i) be limited to 10% or less of the total number of units.

11. An organosiloxane compound according to claim 10 wherein units of the general formula (i) are situated at the end of the organosiloxane compound.

12. An organosiloxane compound according to claim 11 having two end-blocking units of formula (i) and from 8 to 90 units of the general formula (ii).

13. A process for the preparation of the organosilicon compounds of claim 1 which comprises reacting together (A) a compound of the general formula

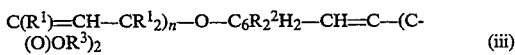
$$C(R^1)\text{==}CH\text{---}CR^1{}_2)_n\text{---}O\text{---}C_6R_2{}^2H_2\text{---}CH\text{==}C\text{---}(C(O)OR^3)_2 \quad (iii)$$

wherein $R^1$ is a hydrogen atom or a $C_{1-5}$ alkyl group, $R^2$ is a hydrogen atom, a $C_{1-5}$ alkyl group or a group $OR^1$, $R^3$ is a $C_{1-5}$ alkyl group and n has a value of from 1 to 6, provided that the group containing the unsaturated triple bond and the two $R^2$ groups are linked to the two meta-positions and to the para-position of the aromatic ring in relation to the group —CH==C—(C(O)OR$^3$)$_2$ and (B) an organosilicon compound having at least one unit of the general formula

$$O_{\frac{3-a}{2}}SiHR_a \quad (iv)$$

any other units present in the organosilicon compounds being those represented by the general formula

$$R_b{}''SiO_{\frac{4-b}{2}} \quad (ii)$$

wherein R represents a $C_{1-8}$ alkyl or aryl group, R" represents a hydrogen atom, a monovalent $C_{1-8}$ hydrocarbon or halogenated hydrocarbon group, a has a value of 0, 1 or 2, b has a value of 0, 1, 2 or 3.

14. A process according to claim 13, wherein stoichiometric proportions of (A) and (B) or a slight stoichiometric excess of (A) are used.

15. A process for the preparation of the organosilicon compounds of claim 1, which comprises submitting a hydrolysable silane of of the formula

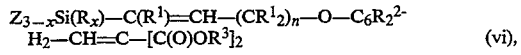
$$Z_{3-x}Si(R_x)\text{---}C(R^1)\text{==}CH\text{---}(CR^1{}_2)_n\text{---}O\text{---}C_6R_2{}^2H_2\text{---}CH\text{==}C\text{---}[C(O)OR^3]_2 \quad (vi),$$

wherein Z is a hydrolyzable group and R, $R^1$, $R^2$, and $R^3$, and n are defined as in claim 1, and x is 0, 1, or 2 to cohydrolysis with a further hydrolysable silane or submitting it to equilibration with a cyclic or linear polydiorganosiloxane exhibiting the units of formula (ii) as given in claim 1.

16. An organosiloxane compound according to claim 1 wherein:

a) at least 80% of all R and R" groups are methyl groups;
b) each $R^1$ is selected from hydrogen, methyl and ethyl;
c) at least one $R^2$ group is a hydrogen, the other being hydrogen, methoxy or ethoxy;
d) $R^3$ is methyl or ethyl;
e) the group $$-C(R^1)=CH-(CR^1{}_2)_n-O-$$

occupies the para-position on the aromatic ring in relation to the group $-CH-C(C(O)OR^3)_2$, and both groups $R^2$ occupy the meta-positions on the aromatic ring in relation to the group $-CH=C(C(O)OR^3)_2$, and;
f) said organosiloxane is a substantially linear or cyclic diorganosiloxane polymer.

* * * * *